United States Patent [19]
Kolb et al.

[11] Patent Number: 5,155,196
[45] Date of Patent: Oct. 13, 1992

[54] POLYMER RESULTING FROM THE CURE OF A PREFORMED CHROMENE-CONTAINING MIXTURE

[75] Inventors: Gerald C. Kolb, Bay City; Daniel M. Scheck, Midland; Stoil Dirlikov, Ypsilanti; Muthiah Inbasekaran; James P. Godschalx, both of Midland, all of Mich.

[73] Assignee: The Dow Chemical Company, Midland, Mich.

[21] Appl. No.: 532,297

[22] Filed: Jun. 1, 1990

Related U.S. Application Data

[63] Continuation-in-part of Ser. No. 215,149, Jul. 5, 1988, abandoned, which is a continuation-in-part of Ser. No. 225,699, Jul. 29, 1988, Pat. No. 4,885,403, which is a continuation-in-part of Ser. No. 56,190, Jun. 1, 1987, abandoned.

[51] Int. Cl.$^5$ .......................................... C08F 224/00
[52] U.S. Cl. .................................. 526/268; 526/247
[58] Field of Search ............... 526/285, 267, 268, 286, 526/289, 247

[56] References Cited

U.S. PATENT DOCUMENTS

| | | |
|---|---|---|
| 3,322,813 | 5/1967 | Seki et al. |
| 3,594,175 | 7/1971 | Hay |
| 3,660,499 | 5/1972 | Kobayashi et al. |
| 3,686,221 | 8/1972 | O'Brien et al. |
| 3,830,849 | 8/1974 | Martin et al. |
| 3,872,104 | 3/1975 | Martin et al. |
| 3,880,935 | 4/1975 | Chodnekar et al. |
| 3,896,042 | 7/1975 | Anderson et al. |
| 3,950,328 | 4/1975 | Karrer |
| 3,957,833 | 5/1976 | Chodnekar et al. |
| 4,005,148 | 1/1977 | Aoki et al. |
| 4,029,649 | 6/1977 | Karrer |
| 4,132,706 | 1/1979 | Doorakian et al. |
| 4,137,329 | 1/1979 | Hangartner et al. |
| 4,138,579 | 2/1979 | Chodnekar et al. |
| 4,151,294 | 4/1979 | Kurmeier et al. |
| 4,186,141 | 1/1980 | Torii et al. |
| 4,226,800 | 10/1980 | Picklesimer |
| 4,314,086 | 2/1982 | Soula et al. |
| 4,338,468 | 7/1982 | Farooq et al. |
| 4,349,567 | 9/1982 | Ackermann et al. |
| 4,356,329 | 10/1982 | Bettarini et al. |
| 4,389,498 | 6/1983 | Seeney et al. |
| 4,496,771 | 1/1985 | Massardo et al. |
| 4,497,727 | 2/1985 | Okamoto |
| 4,540,711 | 9/1985 | Bettarini et al. |
| 4,613,703 | 9/1986 | Hefner, Jr. |
| 4,916,203 | 4/1990 | Pigneri et al. ...................... 528/101 |

FOREIGN PATENT DOCUMENTS

| | | |
|---|---|---|
| 12798 | 7/1980 | European Pat. Off. |
| 0171762 | 2/1986 | European Pat. Off. |
| 3224503 | 1/1984 | Fed. Rep. of Germany |
| 1131285 | 10/1986 | United Kingdom |

OTHER PUBLICATIONS

Vartanyan, R. S., et al. Arm. Khim Zh 1974, Synthesis and hydration of Propargyl ethers and ethynylation of the resulting ethers of hydroxyacetone CA 81:74405r.
Kato, M., Photosensitive resins containing propargyl group, Dec. 18, 197 CA 78:137333r.
Madhukar, et al, Pesticidal Phenyl derivatives Chemical Abstracts, vol. 76, 1972, CA 3563r.
Shikhiev, I. A. et al, Ref. Zh. Khim., 1976, Synthesis of Aromatic-type Acetylenic Ethers and Keto Ethers. CA 85:192273r.
Hlubucek, J., et al, Aust. J. Chem., 1971, (24)11, 2347–54 vol. 75, 1971-151636m Synthesis of 2,2–dimethylchromenes, Heterocyclic Compounds.
34136d, Karrer, Friedrich, Insecticidal Alkenyl Aryl Ethers, Noncondensed Aromatics, vol. 77, 1972.
Starks, C., Liotta, C., Phase Transfer Catalysis, 1978 pp. 1–8, 57–63, and 77–78.
Brock, P., Cox, R., Laminating Resin Compositions, IBM Technical Disclosure Bulletin, vol. 27, No. 4B, Sep. 1984.
Polymer Letters, Photosensitive Polyacetylenes, vol. 8, pp. 97–99.
E. D'Incan, et al, Orientation Del'Alkylation D'Anions, etc., Tetrahedron, vol. 31, No. 2-E pp. 159–164, 1975.
Forshey, et al Potential Hazards of Propargyl Halides and Allene, Fire Technology, vol. 5, pp. 100–111.
M. Harfenist, et al., The Influence on the Rate of Thermal Rearrangement of Aryl Propargyl Ethers to the Chromenes. The gem–Dimethyl Effect J. Org. Chem., vol. 57, No. 6, p. 841 (1972).
W. Anderson and E. LaVoie, Thermal Cyclization of Substituted Aryl Propargyl Ethers. The Scope and Regioselectivity of Reaction in the Synthesis of Substituted 3-Chromenes, J. Org. Chem., vol. 38, No. 22, p. 3832 (1973).
K. K. Balasubramanian and B. Venugopalan, Studies in Claisen Rearrangements Claisen Rearrangement of Bispropargyl Ethers, Tetrahedron Letters, No. 29 pp. 2707–2710 (1973).
S. Powell and R. Adams, A Comparison of the Activity of Certain Unsaturated Groups with the Activity of the Allyl Group in Certain Ethers, J. Chem. Soc., vol. 42, p. 646 (1920).
von J. Zsindely und H. Schmid, Sigmatropische Umlagerungen von Aryl-propargylathern; Synthese von 1,5-Dimethyl-6-methylen-tricyclo [3,2,1,0$^{2,7}$]-oct-3--en-8-Derivaten, Helv. Chim. Acta, 51, 1510 (1068).
von Ursula Koch-Pomeranz, et al., Die durch Silberionen katalysierte Umlagerung von Propargyl--phenylather, Helv. Chim. Acta, 56 2981 (1973).
Balasubramanian, Reddy and Nagarajan, A Novel Mecuric Ion Catalysed Reaction of 1,6-Diaryloxy-2,-4-Hexadiynes to 4–4'-Bichromenes, Tetrahedron Letters, 50, 5003 (1973).

*Primary Examiner*—Christopher Henderson

[57] ABSTRACT

This invention relates to a solvent process for the conversion of aromatic propargyl ethers into chromenes. The process can be catalyzed with copper or zinc salts. The preferred salt is cuprous chloride. The most preferred solvent is a dichlorobenzene. The invention also relates to chromene products formed using the process and to the polymerization of that chromene product and its polymerized product, the latter product having substantially improved flexural modulus and flexural strength properties. The polymerized product is also moisture insensitive.

7 Claims, No Drawings

POLYMER RESULTING FROM THE CURE OF A PREFORMED CHROMENE-CONTAINING MIXTURE

RELATED APPLICATIONS

This application is a continuation-in-part of application Ser. No. 215,149, filed Jul. 5, 1988, now abandoned, which was a continuation-in-part of application Ser. No. 225,699, filed Jul. 29, 1988, which issued as U.S. Pat. No. 4,885,403 on Dec. 5, 1989, which was a continuation-in-part of application Ser. No. 56,190 to Inbasekaran, et al., filed Jun. 1, 1987, now abandoned.

FIELD OF THE INVENTION

This invention relates to a method of preparing and polymerizing chromenes derived from particular propargyl ethers. More particularly, this invention relates to (1) a process for preparing chromene mixtures by heating aromatic propargyl ethers in an appropriate solvent; (2) a process for polymerizing such preformed chromene-containing mixtures; and (3) the products formed from each of these processes. The polymers of this invention are utilized in high temperature composites and electrical laminates.

BACKGROUND OF THE INVENTION

The invention relates to a solvent process for preparing thermosetting compositions containing polymerizable chromenes derived from aromatic propargyl ethers. The polymerized products exhibit an unexpected substantial improvement in the flexural modulus and flexural strength, compared to other state of the art thermoset resins.

U.S. Pat. No. 4,226,800 to Picklesimer teaches the direct polymerization of propargyl ethers to polymers. It reports a process wherein a phenolic material is reacted with propargyl bromide in aqueous sodium hydroxide solution to afford propargyl ethers. The resultant ethers are then thermally polymerized without solvent directly to hard polymers.

IBM Technical Disclosure Bulletin, Vol. 27, No. 4B, pp. 25-29, (September, 1984), also describes the direct polymerization of polypropargyl ethers to polymers. Specifically, the bulletin describes that a mixture containing a 1:1 ratio by weight of aromatic propargyl ethers:

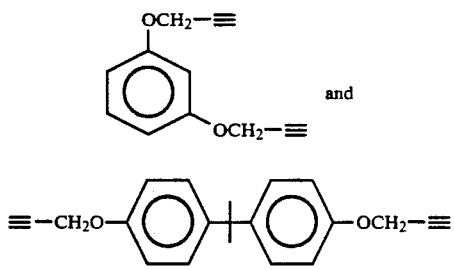

can be polymerized by heating at 130° C. for several minutes and then at 250° C. for at least an hour. The process described to prepare the propargyl ethers utilizes propargyl bromide.

M. Harfenist and E. Thom, in *The Influence Of Structure On The Rate Of Thermal Rearrangement Of Aryl Propargyl Ethers To The Chromenes*, J. Org. Chem; Vol. 37, No. 6, p. 841 (1972), describe the cyclization of monofunctional propargyl ethers to monofunctional chromenes in yields of 36 to 76 percent, by heating in a solvent such as dimethylaniline, trimethylene glycol, or dichlorobenzene.

W. Anderson and E. LaVoie, in *Thermal Cyclization Of Substituted Aryl Propargyl Ethers. The Scope And Regioselectivity Of The Reaction In The Synthesis Of Substituted 3-Chromenes*, J. Org. Chem., Vol. 38, No. 22, p. 3832 (1973), describe the thermal cyclization of substituted aryl propargyl ethers. Specifically, they report the cyclization of simple 3-aryloxypropynes to the corresponding chromenes in approximately 60 percent yield, using the solvent diethylaniline at temperatures between 210° C. and 215° C.

K. Balasubramanian and B. Venugopalan, in *Studies in Claisen Rearrangements: Claisen Rearrangement of Bispropargyl Ethers*, Tetrahedron Letters, No. 29, p. 2707, (1973), report the formation of bischromenes derived from the bispropargyl ethers of 2,7-dihydroxynaphthalene and hydroquinone by heating the latter compounds in N,N-diethylaniline.

S. Powell and R. Adams, in *A Comparison of the Activity of Certain Unsaturated Groups with the Activity of the Allyl Group in Certain Ethers*, J. Chem. Soc., Vol. 42, p. 646 (1920), report that phenyl and p-bromophenyl propargyl ethers decompose upon heating with or without a solvent to tarry mixtures.

In addition to solvent systems for chromene preparation, catalytic processes are also known. Zsindely and Schmid, in *Sigmatropische Umlagerungen von Arylpropargylathern; Synthese von 1,5-Dimethyl-6-methylenetricyclo [3,2,1,0$^{2,7}$]-oct-3-en-8-on Derivaten*, Helv. Chim. Acta, 51, 1510 (1968), disclose the rearrangement of aromatic propargyl ethers to chromenes at temperatures of about 200° C. Koch-Pomeranz, Hansen, and Schmid, in *Die Durch Silberionen Katalysierte Umlagerung von Propargyl-phenylather*, Helv. Chim. Acta, 56, 2981 (1973) demonstrate that this rearrangement is catalyzed by silver tetrafluoroborate or silver trifluoroacetate provided at between 45 and 330 mole percent. According to the authors, such catalysts enable the reaction to be carried out at lower temperatures (20° C. to 80° C.) using a benzene or chloroform solvent.

Balasubramanian, Reddy and Nagarajan, in *A Novel Mercuric Ion Catalyzed Reaction of 1,6-Diaryloxy-2,4-Hexadiynes to 4-4'-Bichromenes*, Tetrahedron Letters, 50, 5003 (1973), report the mercuric oxide and concentrated sulfuric acid catalyzed rearrangement of bispropargyl ether:

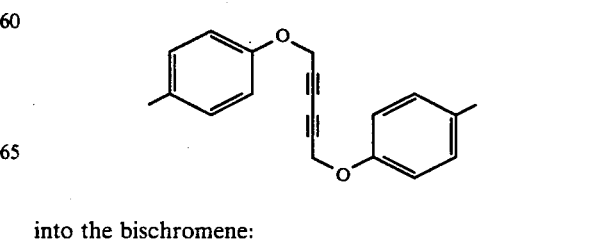

into the bischromene:

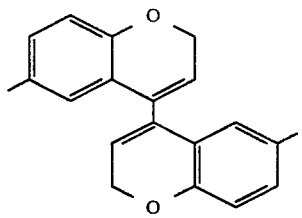

They obtained the bischromene in 61 percent yield as crude, impure material which had to be purified by column chromatography.

The prior art poses several disadvantages. First, U.S. Pat. No. 4,226,800 and the IBM Technical Disclosure Bulletin describe highly exothermic direct polymerization processes, i.e., the heats of polymerization exceed 1100 Joules per gram. Such high heats of polymerization lead to an undesirable inclusion of voids in the polymer and thermal stresses, which deleteriously affect the resultant polymer.

Second, known methods of preparing chromenes contemplate the complete conversion of propargyl ethers thereto. Harfenist and Thom suggest this attempted complete conversion leads to deleterious tar formation and a resultant loss of yield.

Third, the prior art fails to utilize preferred catalysts. The Koch-Pomeranz process utilizes silver salts, which are expensive and which may lead to the formation of undesirable byproducts, e.g., benzofurans. The Balasubramanian process utilizes mercuric salts, which are toxic and raise environmental concerns. U.S. Pat. No. 4,226,800 and the IBM Technical Bulletin utilize propargyl bromide, which is relatively expensive, inaccessible on a commercial scale, and shock sensitive, according to *Fire Technology*, 5, 100 (1969).

Those in the industry would find great advantage in the following: (1) a polymer with excellent physical properties produced through a reaction having a relatively low heat of polymerization; (2) reactions which enjoy high product yields without substantial tar formation; and (3) reactions which utilize preferred catalysts.

SUMMARY OF INVENTION

Accordingly, this invention overcomes the above-identified problems by providing an inventive chromene-containing mixture, a process for its preparation, a process for its polymerization, and the polymerization product thereof.

Specifically, this invention relates to a chromene-containing mixture of monomers, said monomers comprising compounds corresponding to Formula (I):

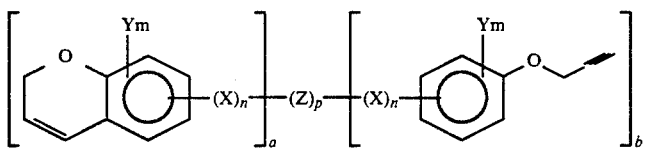

where X is

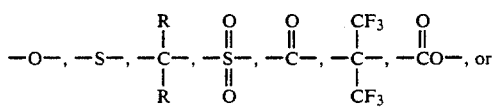

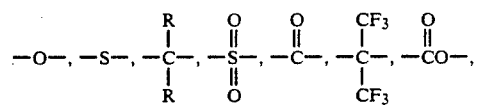

$Y$ is independently at each occurrence a halogen, $-OR$, $-NO_2$, $-NH_2$, a $C_1$ to $C_4$ hydrocarbon radical, $-SO_2Ar$, $-O_2CR$, or $-CN$;

$Z$ is

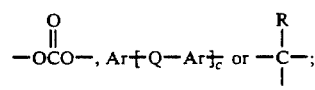

$Ar$ is a $C_6$ to $C_{20}$ aromatic radical optionally substituted with $Y_m$;

$Q$ is

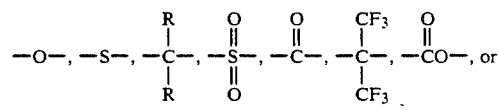

$R$ is independently $Ar$, a $C_1$ to $C_4$ hydrocarbon radical, or $H$;

$c$ is an integer from 0 to 2 inclusive;

$m$ is an integer from 0 to 4 inclusive;

$n$ is 0 or 1;

$p$ is 0 or 1;

$a+b$ equals the valence of $Z$ if $p=1$, and $a+b=2$ if $p=0$; and the average value of "a" within said mixture exceeds 0.

This invention further relates to a process for preparing the above-identified chromene-containing mixture comprising: (a) reacting an aromatic propargyl ether in a suitable solvent at reaction temperature for reaction time, said propargyl ether corresponding to Formula (II):

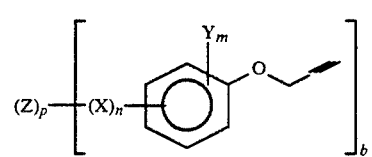

wherein each of the variables is as defined with respect to Formula (I); and (b) recovering a resulting chromene-containing mixture comprising at least 10 percent chromene moiety (I). Preferred solvents comprise diethylbenzene, diisopropylbenzene, dichlorobenzene, trichlorobenzene, tetralin, and mixtures thereof. Preferred reaction temperatures range from 100° C. to 220° C. The process may further utilize a catalyst, such as copper or zinc halide or acetate in appropriate amounts, preferably between 10 ppm and 10,000 ppm, more preferably between 50 ppm and 500 ppm.

This invention further relates to an in situ process for preparing the inventive chromene-containing mixture. The in situ process comprises: (a) reacting a phenolic compound with a propargyl halide in an aqueous solution of an alkaline agent in the presence of a phase transfer catalyst under reaction conditions suitable to produce the above-identified propargyl ether; (b) adding an inert solvent to said propargyl ether, forming a solubilized propargyl ether; (c) purifying said solubilized ether; and (d) reacting said solubilized propargyl ether in a suitable solvent at reaction temperature to form the above-identified chromene-containing mixture.

This invention further relates to a polymer comprising the cured product of the above-identified preformed chromene-containing mixtures, polymerization occurring through at least one chromene moiety. Preferably, the chromene-containing mixture utilized will comprise at least ten percent chromene moiety. Such polymers will preferably be substantially void-free.

This invention further relates to electrical laminates comprising the inventive polymer.

DESCRIPTION OF THE INVENTION

This invention provides a processable, preformed chromene-containing mixture useful to produce substantially moisture insensitive polymers having good physical properties. Throughout this writing, "preformed" means chemically isolated or formed in a discrete step. Thus, a preformed chromene-containing mixture is derived from a propargyl ether, and is or may be isolated, prior to polymerization. In contrast, a "direct" polymerization process comprises polymerizing a propargyl ether without first isolating any chromene moiety bearing compounds.

Converting an aromatic propargyl ether to a preformed low viscosity chromene-containing mixture prior to polymerization affords two principle advantages. First, the low viscosity character of the inventive chromene-containing mixtures facilitates processability. If desired, a higher viscosity product may be attained by B-staging the chromene-containing mixture. Second, the partial conversion of the aromatic propargyl ether moiety into chromene moiety reduces the heat of polymerization. Milder heats of polymerization translate to substantially void-free parts exhibiting minimal shrinkage. The polymers of the subject chromene-containing mixture show excellent electrical and flexural properties up to 450° F. The polymers are moisture insensitive and enjoy a wide range of end uses, e.g., in high temperature composites and electrical laminates.

The several embodiments of this invention are set forth in greater detail below.

Formation of Chromene-Containing Mixtures from Propargyl Ethers

In one embodiment, the invention relates to a solvent process for preparing thermosetting compositions containing polymerizable chromene-containing mixture derived from aromatic propargyl ethers of Formula (II):

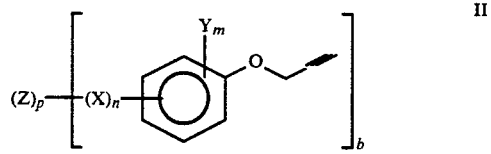

The resultant chromene-containing mixture comprises monomers of Formula (I):

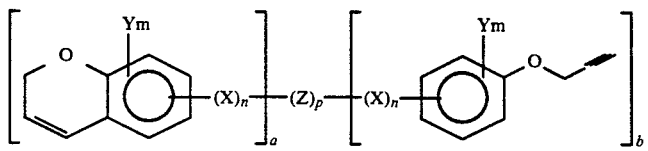

In both Formulas (I) and (II), each of the variables is as defined hereinbefore.

For example, bispropargyl ether of bisphenol A corresponds to Formula (II), wherein n=0, and p=1,

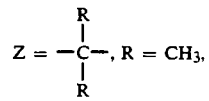

and b=2. Example 1 illustrates the preparation of a compound of this formula. Similarly, a dichromene prepared therefrom corresponds to Formula (I), wherein n, Z, p, and R are similarly defined, a=2, and b=0.

Note the optional presence of the X and Z units. Should the formula include an X unit, n will equal 1. Likewise, should the formula include a Z unit, p will equal 1. Should the formula not include an X unit, n will equal 0. Likewise, should the formula not include a Z unit, p will equal 0.

Formulas (I) and (II) contemplate different valences of Z. Using Formula (I) as an illustration, if the valence of Z is 2, as where Z=—O—, a+b=2. Likewise, if the valence of Z is 3, as where

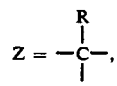

a+b=3. Should Z comprise a chemical bond, i.e., where p=0, a+b=2. Thus, when p=0, Z comprises a chemical bond between two X groups (if n=1) or between the two phenylene rings of the bonded propargyl ether and/or chromene moieties (if n=0). Propargyl ethers corresponding to embodiments where n=p=0 may be prepared in accordance with Example 1 utilizing a commercially available bisphenol starting material.

The provision of $Z=Ar\{Q-Ar\}_c$ contemplates the utilization of, for example, the bispropargyl ether of bisphenol P, which is commercially available. Similarly, the invention contemplates the use of bisphenols wherein $Z=Ar\{Q-Ar\}_c$, $Q=-O-$, and $C=2$. U.S. Patent 3,738,962 to Loudas, et al. discloses such compounds as precursors to cyanates.

The subject solvent process comprises: (1) providing the desired aromatic propargyl ether; and (2) converting the aromatic propargyl ether to a chromene-containing mixture, optionally in the presence of a suitable catalyst.

Propargyl Ether Formation

Suitable aromatic propargyl ethers may be made according to the teaching set forth in U.S. Pat. No. 4,885,403, to Inbasekaran et al, hereby incorporated by reference. Inbasekaran et al teach stirring phenolic material and a propargyl halide in aqueous caustic solution in the presence of a phase transfer catalyst to produce an aromatic propargyl ether. Suitable phase transfer catalysts comprise tetraalkylated ammonium halides, tetraalkylated phosphonium halides or tetraalkylated arsonium halides having an alkyl radical of 1 to 50 carbon atoms or a benzyl group; poly(ethylene glycol), having a molecular weight ranging from 200 to 50,000; poly(ethylene glycol alkyl ether) having a molecular weight ranging from 200 to 50,000; crown ethers; or cryptates. Suitable halides include iodides, bromides, chlorides or fluorides. The caustic solution preferably comprises either a solution of sodium hydroxide or potassium hydroxide. The phenolic material preferably comprises a bisphenolic compound having two aromatic rings. Operating temperatures during the ether synthesis range from 0° C. to 100° C., preferably from 20° C. to 50° C.

The examples set forth procedures to make several propargyl ethers suitable to practice the subject invention.

Formation of a Chromene-Containing Mixture from Aromatic Propargyl Ethers

According to the present invention, an aromatic propargyl ether, such as that set forth in formula (I) above, is heated in a solvent at 100° C. to 220° C. for a period of time ranging from 1 to 100 hours, more preferably 2 to 12 hours, under subatmospheric, atmospheric, or superatmospheric pressure. Any suitable solvent can be used. Depending on the boiling point of the solvent, the desired reaction temperature can be maintained by adjusting the pressure under which the reaction is conducted. Preferably, the reaction is conducted under atmospheric pressure and in the temperature range of 100° C. to 220° C., more preferably, 150° C. to 220° C. Therefore, the preferred solvents are those with boiling points in the same temperature range. Specifically, diethylbenzene, diisopropylbenzene, dichlorobenzene, trichlorobenzene, tetralin, and mixtures thereof preferred solvents. The choice of reaction conditions, that is reaction temperature and time, is determined by the desired extent of conversion of aromatic propargyl ether. A longer reaction, or higher reaction temperature will provide a greater conversion. Other reaction conditions are conventional. Removal of the solvent by conventional techniques, for example, distillation at reduced pressures, provides the product in excellent yield.

The desired chromene-containing mixture comprises components represented by formula (I) above. Within a given chromene-containing mixture, only variables a and b will vary. Thus, when the valence of Z is 2, the chromene-containing mixture potentially comprises unreacted bispropargyl ether (when a is 2 and b is 0), monopropargyl ether-monochromene (when a and b are both 1), and dichromene (when b is 2). That is, the chromene-containing mixture derived from the bispropargyl ether of bisphenol A comprises the following entities (IV), (V), and (VI).

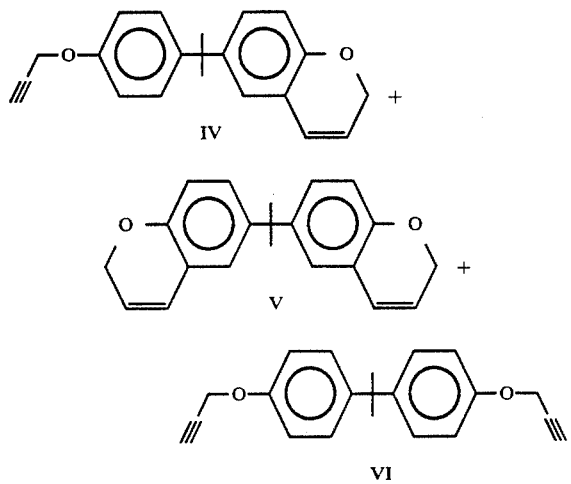

While as defined, each component of a given chromene-containing mixture will comprise identical X and Z moieties, utilization of more than one chromene-containing mixture in a given application may be advantageous. For example, electrical laminate applications require an ignition-retardant product. While non-brominated chromene-containing mixtures derived from the propargyl ether of bisphenol A are subject to combustion, the corresponding brominated species are thought to be ignition retardant. However, the brominated chromene-containing mixture is thought to be more expensive than the non-brominated mixture. Incorporating a small amount of the brominated mixture into the non-brominated mixture before formation of the laminate may provide ignition retardant parts at a decreased cost.

In addition, one can characterize the degree of conversion and the composition of the product mixture by the percentage of chromene moiety therein. The chromene-containing mixture of this invention can vary from 10 percent to 100 percent chromene. A given percentage may be established in an infinite number of ways. For example, a 50 percent chromene mixture may result from the mixture of 50 percent dichromene with 50 percent bispropargyl ether, from 100 percent monopropargyl ether-monochromene, or from any suitable combination therebetween. A given percentage may be obtained by stopping the conversion of the propargyl ether at an appropriate time prior to complete conversion to dichromene. The conversion of propargyl ethers to chromenes can be monitored by gas chromatography.

The selection of an appropriate chromene mixture composition is determined by the desired ease of subsequent polymerization and the desired qualities of the resulting polymer. In general, the higher the chromene content of the preformed mixture, the lower the heat of polymerization. The chromene-containing mixture may comprise from about 10 percent to about 100 percent chromene moiety. Preferably, the chromene-containing mixture will comprise from about 30 percent to about 99 percent chromene moiety, the most preferred range being from about 50 percent to about 99 percent. Herein "percent chromene" means the ratio of chromene moiety to the sum of the chromene and ether moieties within a given mixture.

Catalytic Process

According to another feature of the present invention, an aromatic propargyl ether is heated in a solvent to a temperature between about 100° and about 220° C., more preferably between about 150° and about 185° C. in the presence of about 10 ppm to about 10,000 ppm, more preferably about 50 ppm to about 500 ppm, of a copper or zinc salt for a period of time ranging from about 1 hour to about 100 hours, more preferably about 2 hours to about 12 hours, under subatmospheric, atmospheric or superatmospheric pressure. The catalytic conversion of the bispropargyl ether of bisphenol A (VI) into the mixture of ether VI and chromenes IV and V can be accomplished in substantially less time using 100 ppm copper (I) chloride as catalyst than without catalyst present. The reaction may be expressed as follows:

eliminates steps and makes the process more economical. This single step process also reduces waste levels.

The single-step process involves stirring phenolic material and at least a stoichiometric amount of propargyl chloride in aqueous caustic solution in the presence of a phase transfer catalyst. The catalyst can be a tetraalkylammonium halide, a tetraalkylphosphonium halide, poly(ethylene glycol), poly(ethylene glycol alkyl ether), a crown ether or a cryptate. Operating temperature ranges are from 0° C. to 100° C., preferably 20° C. to 50° C., most preferably 40° C. to 45° C. The preferred catalysts are tetrabutylammonium bromide, tetrabutylphosphonium bromide and the corresponding iodide salts. The most preferred catalyst is tetrabutylammonium bromide.

The preferred ratio of the catalyst to the substrate is 1:100 to 10:100, a preferred range being 2:100 to 5:100. The reaction time depends upon operating temperature. At 45° C., the reaction takes 2 hours to consume most of the starting materials. It is preferred to add an excess of 10 mole percent of propargyl chloride after 2 hours, and permit the reaction to proceed to completion at 45° C. for another two hours.

The next phase of this single-step process involves addition of an inert organic solvent to selectively solubilize the propargyl ether. As explained previously, solvents can have a wide range of boiling points between 100° C. and 220° C. with a preferred range being from

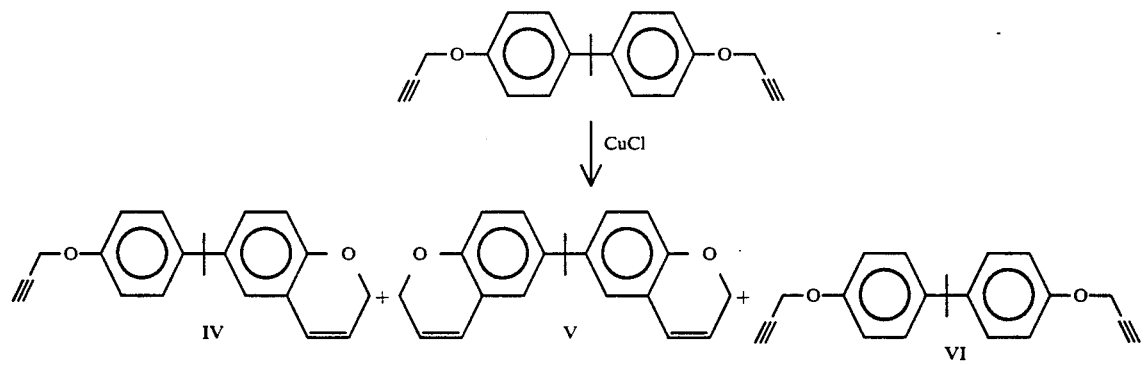

Any suitable solvent can be used. Again, the preferred solvents are dichlorobenzene, trichlorobenzene, diethylbenzene, diisopropylbenzene, tetralin, or mixtures thereof. The most preferred solvent is dichlorobenzene. Any copper (I), copper (II) or zinc (II) salt can be used, but the preferred salts are the halides, acetates, bromides, chlorides, cyanides, fluorides, nitrates, phosphates, sulfates, alkoxides, trifluoroacetates, methanesulfonates, benzenesulfonates, p-toluene sulfonates, tetrafluoroborates, hexafluoroborates, acetylacetonates, gluconates, etc. The most preferred catalyst is cuprous chloride, conveniently used as a solution in concentrated hydrochloric acid. The concentration of the catalyst is from about 10 to 10,000 ppm (0.001 to 1 weight percent), preferably from 50 to 500 ppm (0.005 to 0.05 weight percent).

Formation of Chromene-Containing Mixtures Directly from Bisphenol A

Another embodiment of the present invention relates to the formation of chromene-containing mixtures in a single step from, e.g., bisphenol A and propargyl chloride, without isolating aromatic propargyl ethers. This 150° C. to 220° C. The preferred solvents are diethylbenzene, diisopropylbenzene, dichloro- and trichlorobenzene, decalin, tetralin, and mixtures thereof. The most preferred solvent is orthodichlorobenzene. The solution of propargyl ether in the added solvent separates from the aqueous layer.

The third phase of the present process involves purification of the solution of propargyl ether. Small amounts of undesirable basic impurities such as sodium phenates are effectively removed by washing with a dilute aqueous solution of a mineral acid such as hydrochloric, sulfuric or nitric acid or a carboxylic acid such as acetic acid or by passing through a column of cation exchange resin such as DOWEX MSC-1 (Trademark of The Dow Chemical Company). The latter process is preferred over the former because the ion exchange resin also acts as a desiccant and removes water effectively from the organic solution of propargyl ether. The cation exchange resin is washed with small amounts of an inert solvent such as toluene, benzene, chlorobenzene, dichlorobenzene, and the like to free any residual propargyl ether. Gas chromatography analysis of the organic solution shows the purity of the desired propargyl ether to be 97 to 98 percent.

Conversion of the solution of propargyl ether into the chromene-containing mixture is carried out as taught above. The most preferred catalyst for this conversion is a solution of cuprous chloride in concentrated hydrochloric acid. Fifty (50) to 100 ppm of the catalyst is added. The solution is heated to reflux with the collection of volatile materials (for example, propargyl chloride used in excess, toluene used for washing, etc.). The reflux is carried out for 1 to 24 hours, preferably 2 to 8 hours and most preferably 3 to 5 hours. Progress of the conversion is monitored by gas chromatography. When the most preferred composition of the chromene-containing mixture containing 50 to 99 percent chromene moiety is achieved, the reaction is stopped. The solvent is removed under reduced pressure. The chromene-containing mixture is obtained in 90 to 95 percent yield based on the starting phenolic material.

The process is depicted by the preparation of the chromene-containing resin containing the species, VI, IV and V starting from bisphenol A and propargyl chloride.

The polymerization of the chromene-containing mixtures is typically conducted in a mold of the desired shape in the temperature range of 180° to 250° C. It is desirable to carry out the polymerization in a stepwise manner in which the polymerizable mixture is heated at 180° C. for a period of time and then at 205° C. for another period of time. The polymer can then be removed from the mold and further heated (post-cured) at 250° C. until all the polymerizable groups are substantially converted. The resulting polymer is typically strong, stiff, and highly resistant to water, organic solvents and heat, and can be used as a structural material. The polymerizable mixture can be advantageously combined with fillers, reinforcements, or continuous fibers known to those skilled in the art before polymerization.

The substantial insolubility and infusibility of the inventive polymers renders identification of their chemical structures difficult. We believe, however, that polymerization occurs through the chromene double bond as outlined in the equation below.

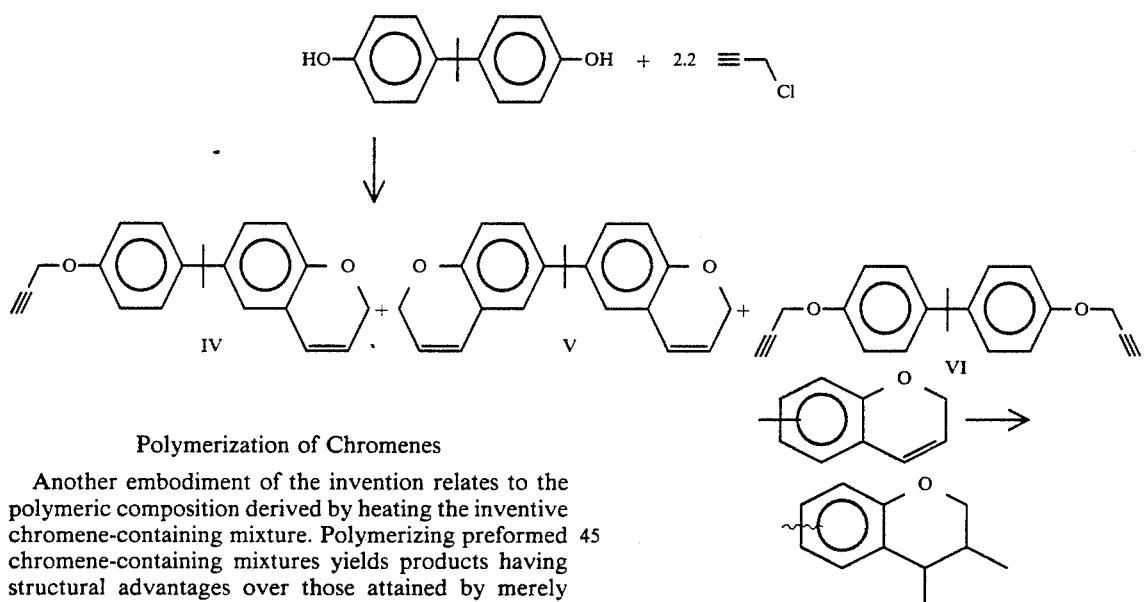

Polymerization of Chromenes

Another embodiment of the invention relates to the polymeric composition derived by heating the inventive chromene-containing mixture. Polymerizing preformed chromene-containing mixtures yields products having structural advantages over those attained by merely heating propargyl ethers until polymerization occurs. Namely, the former process, unlike the latter, provides substantially void-free parts. Such parts exhibit superior mechanical properties, e.g. flexural strength and modulus. The percentage of voids may be determined by density measurements made in accordance with techniques known by those skilled in the art. Preferably, the void percentage will be less than 10 percent, with percentages less than 5 percent being more preferred. Preferably, the flexural strength and modulus of the inventive polymers will be greater than 10 ksi and 400 ksi respectively, with flexural strengths and moduli exceeding 12 ksi and 500 ksi respectively being more preferred. Of course, those skilled in the art will recognize that desired flexural properties vary with the end use contemplated. Thus, while in composite applications a relatively high modulus may be preferred, e.g. 400 ksi, in adhesive applications a relatively low modulus may be preferred, e.g. 200 ksi. In accordance with standard terminology, 1 ksi equals 1000 psi. Also, 1 psi equals $6.897 \times 10^{-3}$ megapascals.

We recognize the possibility that isomerization of the chromene double bond may occur and that this isomerized product and/or the uncyclized propargyl ether may polymerize or copolymerize with the chromene to some, but minor, extent. As the polymerization of the chromene functions takes place, the propargyl ether moieties are simultaneously converted to the chromenes.

The invention will now be described with reference to the following examples. Concentrations are percent by weight unless otherwise specified. These examples are exemplary only and are not intended to be limiting.

EXAMPLE 1

Preparation of Aromatic Propargyl Ethers

The following illustrates the general method of preparation of the subject ether reactant. Forty-five point six (45.6) grams of bisphenol A (0.2 moles), 200 milliliters of 20 percent aqueous sodium hydroxide, and 3.22 grams of tetrabutylammonium bromide (0.01 moles) are combined at 20° C. To this mixture at 20° C., 34.27 grams of propargyl chloride (0.46 moles) is added over a 10 minute period, and the mixture is stirred overnight at room temperature for 16 hours. This produces white crystals that are filtered, washed two times with 200 milliliters of water and two times with 50 milliliters of isopropanol. This produces the desired bispropargyl ether. The bispropargyl ether weighs, after drying, about 58 grams, for a yield of about 95 weight percent. Also it has a melting point of about 83° C. and a purity, as measured by gas chromatography, of about 99 percent.

This example proceeds according to the following formula:

Bisphenol A + 2.3 HC≡C—CH₂Cl + NaOH + H₂O

| Room Temperature,
| 16 hrs., N⁺Bu₄Br⁻
↓

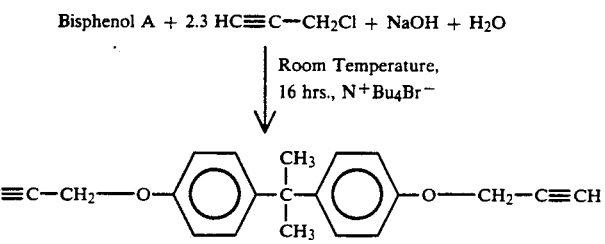

Due to the high purity of the product, no recrystallization is necessary to recover it.

EXAMPLE 2

Example 1 is repeated. However, the reactants are stirred at 50° C. for a period of 4 hours, and 2 to 5 mole percent of tetrabutylammonium bromide is used as the phase transfer catalyst. This produces 85 to 97 percent yield of bispropargyl ether having greater than 98 percent purity. Accordingly, no recrystallization is necessary to recover the bispropargyl ether.

Similar experiments can be conducted which give the following propargyl ethers:

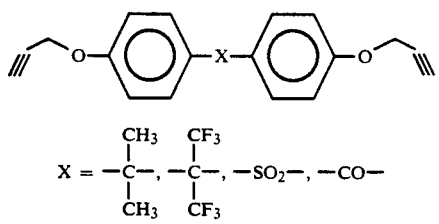

$$X = -\underset{\underset{CH_3}{|}}{\overset{\overset{CH_3}{|}}{C}}-, -\underset{\underset{CF_3}{|}}{\overset{\overset{CF_3}{|}}{C}}-, -SO_2-, -CO-$$

EXAMPLE 3

Formation of a Chromene-containing Mixture From The Bispropargyl Ether of Bisphenol A A mixture of the propargyl ether of bisphenol A (500 grams) and 2.20 liters of DOWTHERM J (Trademark of The Dow Chemical Company for a mixture of isomers of diethylbenzene) are stirred and heated under gentle reflux with a nitrogen blanket for 42 hours. Analysis of an aliquot by gas chromatography (narrow bore capillary column, 15 meters, bonded with 0.25 micrometers DB-5) shows about 41 percent bischromene, 43 percent monochromene-monopropargyl ether and 14 percent bispropargyl ether. Most of the solvent is distilled off under reduced pressure and complete removal of solvent is effected by Wiped Film distillation. The dark red liquid resin (about 460 grams) containing about 63 percent chromene is analyzed by gas chromatography using an internal standard (1-phenyl decane) and is found to have substantially no oligomers. A dynamic scanning calorimetry run shows an exotherm of about 460 joules/gram.

EXAMPLE 4

Formation of a Chromene-containing Mixture From The Bispropargyl Ether of Hexafluorobisphenol A

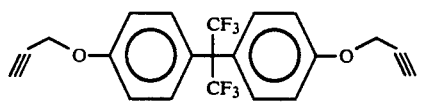

A mixture of the bispropargyl ether of hexafluorobisphenol A (179.4 grams) and 500 milliliters of 1,2,4-trichlorobenzene is stirred and heated under reflux with a nitrogen blanket for 8 hours. Gas chromatographic analysis of an aliquot shows about 44 percent monochromene, 38 percent bischromene and 16 percent bispropargyl ether of hexafluorobisphenol A. Solvent is removed as described in Example 3 and the dark red resin (about 179 grams) containing about 60 percent chromene shows an exotherm of about 400 joules/gram.

EXAMPLE 5

Formation of a Chromene-containing Mixture From The Bispropargyl Ether of Bisphenol S

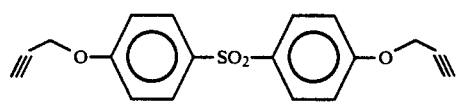

A mixture of the bispropargyl ether of bisphenol S (50 grams) and 150 milliliters of 1,2,4-trichlorobenzene is stirred and heated under reflux with a nitrogen blanket for 16 hours. After the removal of solvent, the dark red resin containing about 62 percent chromene is used for polymerization.

EXAMPLE 6

Formation of a Chromene-containing Mixture From The Bispropargyl Ether of Bisphenol K

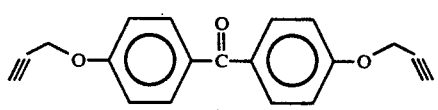

A mixture of the bispropargyl ether of bisphenol K (72 grams) and 220 milliliters of trichlorobenzene is stirred and heated under reflux with a nitrogen blanket for 14 hours. Removal of solvent provides the dark red resin containing about 60 percent chromene.

EXAMPLE 7

Formation of a Chromene-containing Mixture From The Bispropargyl Ether of Thiodiphenol

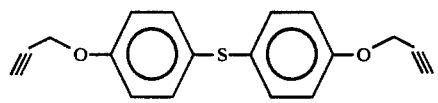

Synthesis of the bispropargyl ether of thiodiphenol 4,4'-Thiodiphenol (43.65 grams, 0.20 moles), NaOH (125 milliliters of a 5N aqueous solution, 0.625 moles) and tetrabutylammonium bromide (2.0 grams, 0.0062 moles) are combined in a 500 milliliter flask. To this mixture, propargyl chloride (29.8 grams, 0.40 moles) is added. The mixture is heated to reflux with stirring for 10.5 hours. Additional propargyl chloride (3.2 grams, 0.04 moles) is added after refluxing 2 hours. The mixture is neutralized with concentrated hydrochloric acid, and the oily product is extracted with 100 milliliters methylene chloride. The aqueous layer is extracted with additional methylene chloride, then the organic layers are combined, dried, filtered and solvent is removed on a rotary evaporator. The crude product is a viscous dark reddish liquid and weighs about 54 grams. The crude product is extracted two times with 200 milliliters cyclohexane. The combined cyclohexane extracts are filtered and the solvent is removed using a rotary evaporator. The product obtained weighs about 15 grams, reflecting about a 26 percent yield. Infrared and nuclear magnetic resonance spectra confirm the light yellow liquid to be the desired bispropargyl ether. The purity as measured by gas chromatography is about 91 percent. A dynamic scanning calorimetry run shows an exotherm of about 1200 joules/gram.

Synthesis of chromene-containing mixture

A mixture of the bispropargyl ether of thiodiphenol (8.0 grams), 25 milliliters o-dichlorobenzene and 0.007 milliliters of CuCl solution (1 gram CuCl/4 milliliters concentrated hydrochloric acid) is stirred and heated under a nitrogen blanket to reflux temperature. After 7 hours of heating at reflux temperature, analysis by gas chromatography shows a composition of about 28 percent bischromene, 39 percent monochromene-monopropargyl ether and 17 percent bispropargyl ether. The mixture is filtered and the solvent removed to yield about 8 grams of a dark red viscous liquid containing about 48 percent chromene. A dynamic scanning calorimetry run shows an exotherm of about 770 joules/gram.

EXAMPLE 8

Formation of a Chromene-containing Mixture From the Monopropargyl Ether of Hydroquinone

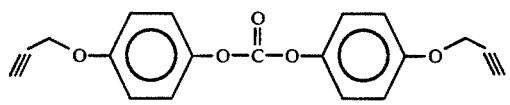

Synthesis of hydroquinone monopropargyl ether

Hydroquinone (75.0 grams, 0.681 moles) is dissolved in 395 milliliters dimethylsulfoxide. The flask is purged with nitrogen, and aqueous sodium hydroxide (275 milliliters of a 5N solution, 1.375 moles) and water (210 milliliters) are added. Propargyl chloride (50.0 milliliters, 51.5 grams, 0.691 moles) is then added and the solution is stirred at room temperature overnight. The aqueous solution is washed twice with toluene, and then is acidified with 65 milliliters concentrated hydrochloric acid. The solution is extracted ten times with 100 milliliters toluene. The combined organic extracts are washed with 200 milliliters water and dried. Solvent is evaporated off and the crude product is distilled under vacuum. The boiling range of a fraction collected is between about 100° C. and about 109° C. at pressures between about 0.4 and 0.5 millimeters of mercury. The yield of monopropargyl ether is about 53 grams reflecting a yield of about 52 percent. Gas chromatography analysis shows no other products present.

Synthesis of 4,4'-bis(propargyloxy)diphenylcarbonate

The monopropargyl ether of hydroquinone (17.2 grams, 0.116 mole), pyridine (9.2 grams, 0.116 mole) and 75 milliliters methylene chloride are charged into a 250 milliliter reactor equipped with a stirrer, nitrogen inlet, addition funnel and thermometer. The mixture is cooled to a temperature between about 0° C. and −10° C. with an ice bath. Trichloromethyl chloroformate (6.3 grams, 0.032 moles) is added over 1.25 hours, keeping the temperature below 0° C. The reaction mixture is allowed to warm to room temperature overnight. Water (75 milliliters) is added slowly to the reaction mixture. The layers are separated and the aqueous layer is extracted twice with 50 milliliters methylene chloride. The combined organic layers are washed with 10 percent hydrochloric acid, dried, filtered, and the solvent is removed on a rotary evaporator. The crude product is washed twice with 100 milliliters isopropanol, filtered and dried at 60° C. overnight in a vacuum oven. The yield of the purified product is about 15 grams, reflecting a yield of about 78 percent. The product is about 97 percent pure as determined by gas chromatography analysis. A dynamic scanning calorimetric run shows an exotherm of about 1190 joules/gram. The melting point is about 107° C.

Synthesis of chromene-containing mixture

A mixture of 4,4'-bis(propargyloxy)diphenylcarbonate (10.0 grams), 50 milliliters o-dichlorobenzene and 0.010 milliliters CuCl solution (1 gram CuCl/4 milliliters concentrated hydrochloric acid) is stirred and heated under a nitrogen blanket to reflux temperature. After 30 hours of heating at reflux, analysis by gas chromatography shows a composition of about 37 percent bischromene, 41 percent monochromene-monopropargyl ether and 13 percent bispropargyl ether. The mixture is filtered and the solvent removed to yield between about 9 and 10 grams of a dark red viscous liquid containing about 64 percent chromene. A dynamic scanning calorimetric run shows an exotherm of about 338 joules/gram.

EXAMPLE 9

Formation of a Chromene-containing Mixture From Bisphenol A bis(4-propargyloxybenzoate)

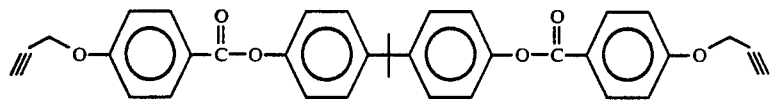

Synthesis of 4-propargyloxybenzoyl chloride

Sodium methoxide (33.6 grams, 0.622 moles) and methyl p-hydroxybenzoate (95 grams, 0.624 moles) are dissolved in 430 milliliters tetrahydrofuran under nitrogen. Propargyl chloride (50 milliliters, 51.4 grams, 0.69 moles) is added and the mixture is refluxed for three days. The reaction mixture is cooled to room temperature and filtered, and solvent is removed by evaporation. The product is dissolved in toluene and washed with 1N NaOH, then with water. The organic solution is dried and the solvent is removed by evaporation. The crude product is recrystallized from refluxing hexane to give about 73 grams of white crystals of the product, which reflects a yield of about 61 percent. The product is substantially pure, as established by nuclear magnetic resonance spectra and gas chromatography analysis.

A mixture of the ester prepared above (39 grams, 0.205 moles), aqueous NaOH (82 milliliters of a 2.56M solution, 0.210 moles), and methanol (250 milliliters) is refluxed for 2 hours. The solution is cooled to room temperature and the solvent is removed by evaporation. The solid is dissolved in water and the aqueous solution is washed with toluene and acidified with concentrated hydrochloric acid. The resulting precipitate is filtered, rinsed with water, and dried under vacuum. The yield of 4-proparglyoxybenzoic acid is quantitative.

The 4-proparglyoxybenzoic acid prepared above is combined with thionyl chloride (100 grams, 0.84 moles), and this mixture is stirred at room temperature overnight. The excess thionyl chloride is distilled out, and the crude product is recrystallized from refluxing hexane. The product is obtained as fine yellow needles which are filtered and dried. About 32 grams of the product are obtained, reflecting an overall yield of about 81 percent for the last two steps. Gas chromatography analysis shows the material to be pure. Nuclear magnetic resonance and infrared spectra are consistent with the expected structure.

Synthesis of bisphenol A bis(4-propargyloxybenzoate)

A solution of 4-propargyloxybenzoyl chloride (17.86 grams, 0.092 moles) in 110 milliliters chloroform is added at room temperature over a 2 hour period to a solution of bisphenol A (9.13 grams, 0.040 moles) and triethylamine (15.0 milliliters, 0.018 moles) in 75 milliliters chloroform. After an additional 1.5 hours, the solution is washed with 5 percent aqueous sodium bicarbonate, then with 1N hydrochloric acid. The organic solution is dried and the solvent is removed by evaporation. The product is purified by recrystallization from a 1:1 solution of toluene in heptane. About 21 grams of product are obtained, reflecting a yield of about 96 percent. Nuclear magnetic resonance spectra confirm the identity of the product, and establish its purity. A dynamic scanning calorimetry run shows a melt endotherm at about 144° C. and a polymerization exotherm with a maximum at about 296° C. The heat of polymerization is about 713 joules/gram.

Synthesis of chromene-containing mixture

A mixture of bisphenol A bis(4-propargyloxybenzoate) (20.7 grams), 65 milliliters o-dichlorobenzene and 0.009 milliliters CuCl solution (1 gram CuCl/4 milliliters concentrated hydrochloric acid) is refluxed with stirring for 53 hours. The solution is then cooled to room temperature and filtered, and the solvent is distilled out under vacuum. A dark brown resin remains. Nuclear magnetic resonance analysis shows the ratio of chromene to propargyl ether to be about 53:47. A dynamic scanning calorimetry run shows a polymerization exotherm with a maximum at aobut 291° C. and a heat of polymerization of about 366 joules/gram.

EXAMPLE 10

Cyclization of Bispropargyl Ether of Bisphenol A

A mixture of bishpenol A bispropargyl ether (16.2 grams), 50 milliliters o-dichlorobenzene and 0.0013 milliliters of CuCl solution (1 gram CuCl/4 milliliters concentrated hydrochloric acid) is heated to temperatures between 170° C. and 175° C. with stirring for 58 hours. Quantitative gas chromatography analysis using an internal standard shows that the mixture contains about 1 percent bispropargyl ether, 5 percent monopropargyl ether-monochromene, and 67 percent bischromene. The oligomer content is thus less than or equal to about 27 percent. The conversion to chromene is about 96 percent.

EXAMPLE 11

A mixture of the bispropargyl ether of bisphenol A (100 grams) and 320 milliliters of tetralin is stirred and heated under refulx with a nitrogen blanket for 6 hours. Gas chromatography analysis of an aliquot shows about 35 percent dichromene, 45 percent monochromene-monopropargyl ether and 17 percent bispropargyl ether. Solvent is removed, as described in Example 3, and the dark red resin (about 95 grams) containing about 58 percent chromene shows an exotherm of about 515 joules/gram, and through gas chromotography, is found to have substantially no oligomers.

EXAMPLE 12

Formation of a Chromene-containing Mixture From Bispropargyl Ether Catalyzed By Cuprous Chloride To a stirred mixture of the bispropargyl ether of bisphenol A (153 grams) and o-dichlorobenzene (445 milliliters) under a blanket of nitrogen is added 60 microliters of a solution of cuprous chloride in concentrated hydrochloric acid (1 gram/4 milliliters) (100 ppm, 0.01 weight percent). The mixture is stirred and heated under reflux for 4 hours. Analysis of a sample of the resin by gas chromatography shows the composition to be about 44 pecent dichromene, 43 percent monochromene-monopropargyl ether, and 13 percent bispropargyl ether. Without catalyst, 36 hours is required to achieve approximately the same conversion.

Thus, the catalyst allows the preparation of low viscosity mixtures containing chromenes from aromatic propargyl ethers by drastically reducing the time necessary for the rearrangement.

EXAMPLE 13

Formation of a Chromene-containing Mixture From Bispropargyl Ether Catalyzed By Cupric Bromide To a stirred mixture the bispropargyl ether of bisphenol A (25 grams) and 75 milliliters o-dichlorobenzene under nitrogen is added 25 milligrams (1000 ppm, 0.1 weight percent) cupric bromide. The mixture is stirred and heated under reflux for 4 hours. Gas chromatographic analysis shows 49 percent of dichromene, 41 percent monochromene-monopropargyl ether, and about 9 percent bispropargyl ether.

EXAMPLE 14

Formation of a Chromene-containing Mixture From Bispropargyl Ether Catalyzed by Zinc Chloride To a stirred mixture of the bispropargyl ether of bisphenol A (110 grams) and 350 milliliters of o-dichlorobenzene under nitrogen is added 110 milligrams (1000 ppm) zinc chloride. The mixture is stirred and heated under reflux for 5 hours. The solvent is removed and the dark red resin (about 109 grams) is recovered. Gas chromatography analysis shows the chromene content to be about 54 percent.

EXAMPLE 15

In situ Formation of a Chromene-containing Mixture From Bisphenol A

A mixture of bisphenol A (146 grams, 0.64 mole) and 400 milliliters of 5N aqueous sodium hydroxide solution is stirred at ambient temperature for 30 minutes. Tetrabutylammonium bromide (6.44 grams, 0.02 mole) and propargyl chloride (92.6 milliliters, 1.28 mole) are added. The mixture is stirred and heated to 45° C. over 30 minutes. After stirring at 45° C. for 2 hours, an additional amount of propargyl chloride (9.26 milliliters, 0.128 mole) is added and heated at 45° C. for another 2 hours. Then, 500 milliliters o-dichlorobenzene and 200 milliliters water is added to the mixture. It is stirred for a few minutes. The o-dichlorobenzene layer is separated and passed through a column of cation exchange resin (DOWEX MSC-1: Trademark of The Dow Chemical Company) (pre-dried at 70° C. for 16 hours under vacuum, 150 gms, 26×3 cm). The column is further washed twice with 100 milliliters toluene. The combined organic solution is placed in a 2 liter 3 neck flask. Forty (40) microliters of a solution of cuprous chloride in concentrated hydrochloric acid (1 gram/4 milliliters) (50 ppm) is added. The mixture is heated to reflux with the overhead collection of volatile liquids. The mixture is refluxed at temperatures between about 185° C. and 186° C. for 4 hours and 50 minutes. Gas chromatography analysis shows the composition contains about 49 percent of the dichromene, about 41 percent of the monochromene-monopropargyl ether, and about 9 percent of the bispropargyl ether. The solvent is removed under reduced pressure. The product is obtained as a dark red, low-viscosity resin weighing about 183 grams, reflecting a yield of about 94 percent. A dynamic scanning calorimetric run shows an exotherm of about 453 joules/gram with the maximum at about 274° C.

Polymerization of the material prepared according to the in situ process, outlined above, proceeds smoothly by heating at 200° C. for 2 hours and at 250° C. for 2 hours leading to a substantially void-free molding with little or no shrinkage.

EXAMPLE 16

Polymerization Of Chromene-containing Mixtures

A chromene-containing mixture prepared as described above in Example 3 is placed in a vacuum oven maintained at a temperature between about 50° C. and 200° C., preferably between 100° C. and 200° C., and most preferably between 170° C. and 180. Vacuum corresponding to about 0.1 millimeter of mercury is applied and the material is degassed for between 10 and 180 minutes, preferably between 60 and 180 minutes, and most preferably between 60 and 120 minutes. The degassed chromene mixture is then carefully poured into a preheated (approximately 170° C.) stainless steel parallel plate mold which is pretreated with TEFLON (Trademark of E. I. du Pont de Nemours & Company) mold release agent. The mold is then placed in a preheated oven and cured according to the desired cure schedule. Typically such a cure schedule would involve heating at moderate temperatures, e.g. between 170° C. and 200° C., until the material gels (2 to 16 hours) then increasing the temperature to finish the cure (200° C. to 250° C,. for 1 to 5 hours). The mold is then cooled slowly and the cured polymer removed. A free standing post-cure at temperature greater than 250° C. for 2 hours is used to increase the glass transition temperature.

Alternatively, triethylenetetramine is added to the degassed chromene mixture at a 0.5 to 2 weight percent level, preferably at a 1 weight percent level prior to pouring into the mold. This improves the moldability of the material and shortens the required cure schedule to about 2 hours at 205° C. followed by about 2 hours at 250° C.

Evaluation of Polymerized Chromene Mixture

A sample cured with 1 percent triethylenetetramine which is cured as described above in Example 16 is evaluated for mechanical, physical, and electrical properties as shown below.

| Properties of Material as Cured* | | |
|---|---|---|
| Property | | |
| Dielectric Constant 10 kHz, dry | 2.93 | |
| % Moisture Uptake Boiling Water, 330 h | 1.7 | |
| Glass Transition Temperature (TMA) | 255° C. | |
| Ultimate Glass Transition Temperature (DMA) | 350° C. | |
| Extrap. Onset of Decomposition (TGA) (nitrogen/air) | 397/405° C. | |
| Flexural Modulus/ksi | Room Temp. | 635 |
| | 149° C. (300° F.) | 486 |
| | 204° C. (400° F.) | 397 |
| Flexural Strength/ksi | Room Temp. | 15.7 |
| | 149° C. (300° F.) | 13.1 |
| | 204° C. (400° F.) | 11.7 |

*The chromene mixture used to prepare the casting was prepared by heating the bispropargyl ether of bisphenol A to reflux in trichlorobenzene for 135 minutes followed by removal of solvent.

While flexural modulus and flexural strength vary with curing schedules these polymers show unexpected improvement over polymers of many state of the art thermoset resins.

Although the invention has been described in conjunction with specific embodiments, it is evident that many alternatives and variations will be apparent to those skilled in the art in light of the foregoing description. For example, a person of ordinary skill in the art can use conventional processing conditions for any of the processes described in this disclosure. Accordingly, the invention is intended to embrace all of the alternatives and variations that fall within the spirit and scope of the appended claims.

What is claimed is:

1. A polymer resulting from the cure of a preformed chromene-containing mixture of monomers of the formula:

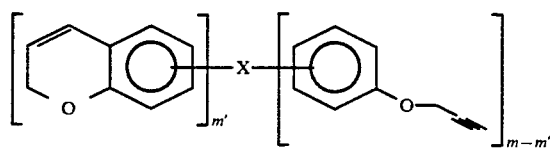

wherein X is absent, —S—, —O—, —C(CH$_3$)$_2$—, —C(CF$_3$)$_2$—,

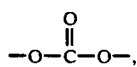

—SO$_2$—, or —CO—, m is 2 and m' is 0, 1, or 2, wherein the average value of "m'" within said mixture is greater than about 0.2, and polymerization occurs through at least one chromene radical.

2. The polymer of claim 1, having a flexural modulus of about 630 ksi.

3. The polymer of claim 1, having a flexural strength of about 14 ksi.

4. The polymer of claim 1, wherein said polymer is substantially insoluble.

5. The polymer of claim 1, wherein said polymer is substantially infusible.

6. The polymer according to claim 1, wherein X is —C(CH$_3$)$_2$— and m is 2.

7. The polymer of claim 1, wherein said polymer is substantially void-free.

* * * * *